United States Patent [19]

DeBoer et al.

[11] Patent Number: 4,733,090

[45] Date of Patent: * Mar. 22, 1988

[54] SCREENS FOR STORING X-RAY IMAGES AND METHODS FOR THEIR USE

[75] Inventors: Charles D. DeBoer; George W. Luckey, both of Rochester, N.Y.

[73] Assignee: Eastman Kodak Company, Rochester, N.Y.

[*] Notice: The portion of the term of this patent subsequent to Jan. 20, 2004 has been disclaimed.

[21] Appl. No.: 891,797

[22] Filed: Aug. 1, 1986

Related U.S. Application Data

[60] Division of Ser. No. 721,130, Apr. 8, 1985, Pat. No. 4,637,898, which is a continuation of Ser. No. 238,404, Feb. 26, 1981, abandoned.

[51] Int. Cl.$^4$ .............................................. G01T 1/105
[52] U.S. Cl. .................................. 250/484.1; 250/487.1
[58] Field of Search ............... 250/484.1, 483.1, 486.1, 250/327.2; 252/301.4 H, 301.36

[56] References Cited

U.S. PATENT DOCUMENTS

| | | | |
|---|---|---|---|
| 3,023,313 | 2/1962 | De La Mater et al. | 252/301.4 H |
| 3,214,622 | 10/1965 | D'Errico et al. | 252/301.36 X |
| 3,859,527 | 1/1975 | Luckey | 250/327.2 |
| 4,079,258 | 3/1978 | Franz et al. | 252/301.4 H X |
| 4,184,077 | 1/1980 | Washida et al. | 250/483.1 |
| 4,261,854 | 4/1981 | Kotera et al. | 250/327.1 |
| 4,599,539 | 7/1986 | Ishizuka et al. | 252/301.36 |
| 4,637,898 | 1/1987 | DeBoer et al. | 250/483.1 |

FOREIGN PATENT DOCUMENTS

| | | | |
|---|---|---|---|
| 703014 | 2/1941 | Fed. Rep. of Germany | 252/301.4 H |
| 2928246 | 1/1980 | Fed. Rep. of Germany | 250/327.2 |
| 2951501 | 7/1980 | Fed. Rep. of Germany | 250/327.2 |
| 796654 | 6/1958 | United Kingdom | 252/301.4 H |
| 536216 | 2/1977 | U.S.S.R. | 252/301.4 H |

OTHER PUBLICATIONS

Reisfeld et al., J. Optical Society of America, vol. 61, No. 10, pp. 1422, 1423, (10/71).
Electroplating Engineering Handbook by Graham et al., Second Edition, p. 427, published by Reinhold Publishing Corporation, New York, (1962).
The Particle Atlas by McCrone et al., pp. 65–76, published by Ann Arbor Sci. Pub., Inc., (1967).
Swank, *Applied Optics*, 12, 1865–1870, (1973).
Gasper, *J. Opt. Soc. Am.*, 63, 714–720, (1973).

*Primary Examiner*—Janice A. Howell
*Assistant Examiner*—Richard Hanig
*Attorney, Agent, or Firm*—Carl O. Thomas

[57] ABSTRACT

A method of storing an image produced by x-ray exposure and releasing the stored image is disclosed. It is disclosed to expose an x-ray storage screen, comprised of an isotropic storage phosphor and a polymer coated on a support, to x-radiation of a first wavelength in an imagewise manner to store an image pattern in the storage screen. The image pattern is retrieved from the storage screen by exposing the storage screen to radiation of a second wavelength, thereby stimulating radiation of a third wavelength. The polymer has an index of refraction which matches the index of refraction of the phosphor at the second wavelength, and the support is non-reflective to radiation of the second wavelength.

14 Claims, No Drawings

SCREENS FOR STORING X-RAY IMAGES AND METHODS FOR THEIR USE

This is a division of copending commonly assigned Ser. No. 721,130, filed Apr. 8, 1985, now U.S. Pat. No. 4,637,898 which is a continuaton of U.S. Ser. No. 238,404, filed Feb. 26, 1981, now abandoned.

BACKGROUND OF THE INVENTION

1. Field of the Invention

This invention relates to x-ray storage phosphor screens, also sometimes referred to as stimulable phosphor sheets or panels, and to methods for their use.

2. Description Relative to the Prior Art

Transparent x-ray screens comprising alkali halide, alkaline earth halide, metal sulfide, and metal selenide phosphors having been prepared by various methods. These transparent screens have been shown to be desirable, because they make more efficient use of impinging x-ray radiation than thick conventional scattering screens, which "waste" a material amount of the radiation in diffusion of the light emitted near the back of the screen and internal absorption. Thick transparent screens, having a deceased number of reflections permit this light to reach the front surface of the screen with minimal deflection and to form a sharper image on the photographic film in contact with the screen. A greater proportion of the x-ray energy, absorbed by the phosphor and converted to light, is utilized in producing images without loss of sharpness.

Thin transparent screens, prepared by vapor deposition and containing only a phosphor, have also been made and exhibit lower speeds than scattering screens with equal phosphor coverage. Further, lacking a protective binder, these transparent screens are fragile and highly susceptible to physical damage. Thicker screens have been made by hot pressing but other defects in the manufacture of these large plates render them expensive to prepare.

U.S. Pat. No. 3,023,313, issued Feb. 27, 1962 to De La Mater et al discloses the use of a polymeric binder with a refractive index as close to that of an alkali metal halide phosphor as possible in order to produce x-ray intensifying screens with improved speed. However, because of substantial differences between the refractive index of selected binders and the refractive index of the phosphor, reflecting pigments must be added to the mixture to prevent "blurring of the image" and improve resolution. Thus, these screens are not truly transparent to light, and some decrease in utilization of absorbed x-rays is observed. The screens of De La Mater comprise a support preferably having a highly reflective base coating.

Swank, *Applied Optics*, 12, 1865–1870 (1973) describes the theoretical calculation of modulation transfer function (MTF), related to resolving power, of x-ray intensifying screens comprising transparent phosphors and a black backing. Swank discloses that although the MTF is enhanced when a black backing is used, 50% of the exposing radiation is absorbed by the backing. Thus, the speed of the x-ray intensifying screen is reduced.

Gasper, *J. Opt. Soc. Am.*, 63, 714–720 (1973) describes the computation of theoretical efficiencies and MTFs of various screen receiver systems, and reports that if a dark antihalation undercoat is applied to the back surface of a transparent screen, the MTF is only slightly improved. If, on the other hand, the back surface is made perfectly reflecting, there is degradation of MTF, but the efficiency of the screen is advantageously doubled, as is shown in FIG. 8 of Gasper.

Experimental verification of the Gasper calculations is provided by measuring the MTF of a transparent hot pressed zinc sulfide screen coated with a dyed gelatin undercoat. Excellent agreement was found between the measured and computed MTFs. Gasper concludes that attempts to improve the MTF of a transparent screen result in an undesirable loss of efficiency. Given a choice between slight increases in MTF coupled with undesirable losses in efficiency (with an absorbing undercoat), and great increases in efficiency coupled with only slightly lower MTFs (reflective undercoat), the high efficiency screen with a reflective undercoat is clearly preferred by Gasper.

It is seen that transparent x-ray screens providing high resolution, while maintaining speed and efficiency, and which are resistant to physical damage and are easily and economically manufactured, are extremely desirable.

SUMMARY OF THE INVENTION

In one aspect this invention is directed to a method of storing an image produced by x-ray exposure and releasing the stored image comprising:

exposing an x-ray storage screen, comprised of an isotropic storage phosphor and a polymer coated on a support, to x-radiation of a first wavelength in an imagewise manner to store an image pattern in the storage screen, retrieving the image pattern from the storage screen by exposing the storage screen to radiation of a second wavelength, thereby stimulating radiation of a third wavelength, the polymer having an index of refraction which matches that of the phosphor at the second wavelength, and the support being non-reflective to radiation of the second wavelength.

In another aspect this invention is directed to an x-ray storage screen comprising a support having thereon a fluorescent composition comprising:

(a) a substantially isotropic storage phosphor, the phosphor being excitable by radiation of a first wavelength and, when thereafter the screen is exposed to radiation of a second wavelength, the phosphor emits radiation of a third wavelength; and (b) a polymer, the polymer having an index of refraction which matches that of the phosphor at the second wavelength; and (c) the support being non-reflective to radiation of the second wavelength.

DETAILED DESCRIPTION OF THE PREFERRED EMBODIMENTS

The x-ray storage screens of this invention are closely related to the x-ray intensifying screens disclosed in DeBoer et al U.S. Pat. No. 4,637,898, based on U.S. Ser. No. 721,130, cited above, (hereinafter referred to as the "parent filing") of which this patent application is a division.

The parent filing x-ray intensifying screens are modified for the purposes of this invention so that they are useful in the apparatus and methods for producing images that are described in U.S. Pat. No. 3,859,527, German No. 2,951,501, and German No. 2,928,246. In this modification an essentially isotropic storage phosphor is coated in a binder on a support that has the characteristics described below. The phosphor is excited by a pattern of radiation of a first wavelength. The phosphor is then exposed to radiation of a second wavelength which causes the said storage medium to emit a third wavelength of radiation having an intensity pattern representative of the stored image. The binder used in making this screen matches the index of refraction of the phosphor at the second wavelength and the support for the screen is selected so that it does not reflect the radiation at the second wavelength. The index of refraction of the binder at the third wavelength is preferably selected so that it does not match that of the phosphor and the support of the screen may reflect the radiation at the third wavelength. Thus, the radiation at the third wavelength, which is emitted when the phosphor is irradiated at the second wavelength, is not trapped by total internal reflection nor by the support, but escapes from the screen and is efficiently collected by a photomultiplier tube with appropriate optics or by other photosensors which respond efficiently to the radiation at the third wavelength. Screens of this type are particularly useful for radiography and other applications in which a pattern of high energy radiation is absorbed by the phosphor, then released by scanning the screen with a laser beam that has a wavelength equal to that where the index of refraction of the phosphor and binder are matched and where the support of the screen has minimum reflectance. Ideally, the beam from the laser follows the path of the high energy radiation so that the resolution of the image from the screen is determined by the dimensions of the laser beam. The light released from the phosphor by the laser is collected by an appropriate photosensor, amplified, and the signal displayed on a cathode ray tube or recorded on an image recording medium to form the image. Appropriate phosphors comprise the barium alkaline earth metal fluorohalides of German No. 2,951,516, German No. 2,928,244, and other storage phosphors which have indices of refraction less than about 1.75 in the visible region of the spectrum.

A parent filing x-ray intensifying screen comprises a support having thereon a fluorescent composition comprising:
(a) from 50 to 90 percent by weight of a substantially isotropic phosphor which is excited by x-rays and substantially transparent to light emitted by said phosphor; and
(b) from 10 to 50 percent by weight of a polymer having an index of refraction within 0.02 of the index of refraction of said phosphor over at least 80 percent of the emission spectrum of said phosphor;
said support having an index of refraction equal to or up to 0.05 units higher than the index of refraction of said phosphor and having a reflection optical density of at least 1.7 to light emitted by said phosphor.

Any substantially isotropic phosphor which is excited by x-rays and substantially transparent to the light emitted by the excited phosphor is useful in preparing the fluorescent composition. The term "substantially isotropic phosphor" is used herein to mean a crystalline phosphor having substantially the same optical properties in all directions of the crystal, and that the crystalline phosphor is substantially free from defects, such as cracks and inclusions, which causes scattering of light. Useful phosphors include activated alkali metal halides, such as KCl:Sb, CsBr:Tl, KI:Tl, KBr:Tl, KCl:Tl, RbCl:Tl, RbBr:Tl, and RbI:Tl; alkaline earth halides such as $BaF_2$ and BaFCl; activated alkaline earth halides such as $CaF_2$:Eu, $SrCl_2$:Sm, $SrF_2$:Eu, BaFCl:Sr, Eu, BaFCl:Eu, and $SrF_2$:Sm; activated metal silicates such as $BaSiO_3$:Eu, $CaSiO_3$:Mn and $Zn_2SiO_4$:Mn; mixed metal fluorides such as $KCdF_3$:Mn and $CsCdF_3$:Mn; metal sulfates such as lanthanide-activated metal sulfates such as $BaSO_4$:Sr, Eu, $SrSO_4$:Eu, $BaSO_4$:Eu, $ZnSO_4$:Mn, and $Cs_3SO_4$:Ce; metal gallates such as $ZnGa_2O_4$:Mn, and phosphates such as lanthanide-activated phosphates such as $Ba_2P_4O_7$:Eu and $Ca_3(PO_4)_2$:Ce. Further examples of phosphors are described in U.S. Pat. Nos. 4,100,101, 2,303,963, 3,173,610, 3,163,610, 3,163,603, and 3,506,584 and in R. C. Pastor et al, *Mat. Res. Bull.*, 15, 469–475 (1980). Typical transparent phosphors include RbI:Tl, KI:Tl, BaFCl:Sr, Eu, $BaSO_4$:Sr, Eu, $BaSO_4$:Sr, Eu, $CsCdF_3$:Mn, $BaF_2$, $KCdF_3$:Mn, and $SrF_2$. Preferred phosphors are RbI:Tl; KI:Tl; BaFCl:Sr, Eu, $CsCdF_3$:Mn, $BaSO_4$:Sr, Eu, and $BaSO_4$:Pb.

The above described phosphors are prepared by any conventional method for preparing isotropic phosphors, such as by introducing the anions and cations which form the phosphor into a reaction solution, maintaining an excess of up to one molar of an anion or cation throughout the reaction mixture, preventing local excesses of cations or anions, and thus slowly growing crystals of the phosphor to at least 0.5 micron, as described in U.S. Pat. No. 3,668,142 issued June 6, 1972 to Luckey, which is hereby incorporated by reference. Other methods for preparing isotropic phosphors which are excited by x-rays and substantially transparent to the emitted light, include precipitation at elevated temperatures and super atmospheric pressures described in Ruthruff, U.S. Pat. No. 2,285,464; precipitation followed by firing, fusion, and grinding to the desired particle size; and ignition in the presence of a flux. The method of U.S. Pat. No. 3,668,142 is the preferred method for preparing the isotropic phosphors.

The phosphor crystals are optionally activated to obtain the desired speed by any conventional method of activation. One method is the addition of a solution of a small amount (about 0.05 percent by weight) of the activating ion in a solvent, such as isopropanol, to a vigorously stirred solution of the isotropic host in a solvent, such as water, at very low temperatures ($-30$ to $+20°$ C.), followed by collection of the precipitated activated phosphor.

The substantially isotropic phosphors of the parent filing generally have crystallizing morphologies which are cubic or substantially cubic. The substantially isotropic phosphors of the parent filing generally have crystal sizes in the range from about 1 to about 50 microns, with the size range from about 10 to about 20 microns being preferred.

The novel x-ray intensifying screen includes any polymer having an index of refraction within 0.02 of the index of refraction of the phosphor over at least 80 percent of the emission spectrum.

The selection of the polymer for the parent filing x-ray intensifying screen is dependent on the index of refraction of the selected substantially isotropic phosphor at its emission wavelength. The index of refraction of the phosphor is determined by measuring the transmission spectra of the phosphor mixed with a series of Cargille liquids, as described in "The Particle Atlas", McCrone, Draftz and Delly, Ann Arbor Science Publishers, Inc. (1967), and determining the wavelength at which the index of refraction of the phosphor and the liquid match. A phosphor dispersion curve is obtained by plotting the wavelengths of maximum transmission for the series on the family of Cargille dispersion curves published in "The Particle Atlas" referred to above. The phosphor dispersion curve thus obtained is used directly to find the index of refraction required for the polymer of the parent filing transparent x-ray intensifying screen.

The polymer having the required index of refraction, i.e., an index of refraction within 0.02 of the refraction of the phosphor over at least 80 percent of its emission spectrum, comprises a single polymerized monomer, or the polymer comprises a mixture of two or more polymerized copolymerizable monomers. Generally, the polymer comprises two copolymerizable polymerized monomers, one of which, when polymerized, provides a polymer of higher index of refraction than required, and one which, when polymerized, provides a lower index of refraction than required. The relative proportions of the two monomers are adjusted to provide the required refraction index. Calculated formulations are verified by measuring the transmission curve of a sample coating of the fluorescent composition of the parent filing intensifying screen on a spectrophotometer. A wavelength of maximum transmission which is less than that of the phosphor emission wavelength indicates that the refractive index of the polymeric binder is too low. A wavelength of maximum transmission which is greater than that of the phosphor emission wavelength indicates that the refractive index of the polymer is too high.

Monomers which, when polymerized, provide an index of refraction higher than that of the phosphor selected generally provide an index of refraction above 1.4, preferably in the range of 1.40 to 1.75. Examples of monomers which, when polymerized, provide an index of refraction higher than that of the phosphor selected, and thus can be mixed with monomers having a lower index of refraction to become useful herein, include S-(1-naphthyl carbinyl)thioacrylate, naphthyl acrylate, 1-bromo-2-naphthylacrylate and naphthylmethacrylate. The preferred monomer is S-(1-naphthyl carbinyl)thioacrylate.

Monomers which, when polymerized, provide an index of refraction lower than that of the phosphor generally provide an index of refraction ranging from about 1.40 to about 1.75, preferably in the range from 1.40 to 1.60. Examples of monomers which, when polymerized, provide an index of refraction lower than that of the phosphor selected and thus are useful when mixed with monomers having a higher index of refraction, include copolymerizable ethylenically unsaturated monomers such as acrylates and methacrylates such as methyl acrylate, ethyl acrylate, propyl acrylate, butyl acrylate, butyl methacrylate, and cyclohexyl methacrylate; vinyl esters, amides, nitriles, ketones, halides, ethers, olefins and diolefins as exemplified by acrylonitrile, methacrylonitrile, styrene, α-methyl styrene, acrylamide, methacrylamide, vinyl chloride, methyl vinyl ketone, fumaric, maleic and itaconic esters, 2-chloroethylvinyl ether, dimethylaminoethyl methacrylate, 2-hydroxyethyl methacrylate, N-vinyl succinamide, N-vinyl phthalimide, N-vinylpyrrolidone, butadiene and ethylene. Preferred monomers are acrylates and methacrylates, with cyclohexyl methacrylate being most preferred.

The proportion in which the above described high index and low index monomers are mixed varies widely to provide a polymer having the required index of refraction. The polymerized low index monomer preferably comprises from 5 to 100 mole percent of the resulting polymer, with the range from 15 to 80 mole percent being most preferred. The polymerized high index monomer preferably comprises from 0 to 95 mole percent of the resulting polymer, with the range from 20 to 85 mole percent being most preferred.

In one embodiment, the polymer of the parent filing intensifying screen comprises from 5 to 100 mole percent of recurring units having the formula:

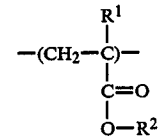

wherein:
$R^1$ is H or alkyl, preferably containing from about 1 to about 4 carbon atoms, such as methyl, ethyl, propyl, isopropyl, and butyl; and
$R^2$ is alkyl, preferably containing from about 1 to about 12 carbon atoms, such as methyl, ethyl, propyl, and butyl; cycloalkyl, such as cyclopentyl and cyclohexyl; aryl preferably containing from about 6 to about 22 carbon atoms, such as phenyl, naphthyl, anthracene, perylene, acenaphthene, and rubrene; aralkyl, preferably containing from about 5 to about 20 carbon atoms, such as benzyl, phenylethyl, phenylpropyl, tolylbutyl, and naphthylmethyl; or aryl substituted with alkyl, preferably containing from about 1 to about 20 carbon atoms, such as methyl, ethyl, isopropyl, and hexyl; alkoxy, preferably containing from about 1 to about 20 carbon atoms, such a methoxy and ethoxy; or heterocyclic, preferably a 5- to 7-membered ring which may be saturated, such as pyrrolidone, morpholine, piperidine, tetrahydrofurane, dioxane, and quinaldine, or unsaturated, such as pyrrole, isoxazole, imidazole, isothiazole, furazan, and pyrazoline.

A preferred polymer of the parent filing x-ray intensifying screen further comprises from 0 to 95 mole percent of recurring units having the formula:

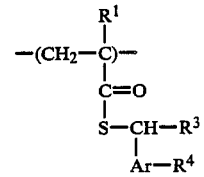

wherein:
Ar is arylene, preferably containing from about 6 to about 22 carbon atoms, such as phenylene, naphthalene, anthracene; perylene, acenaphthene, and rubrene;
$R^1$ is H or alkyl as described for $R^1$ above;
$R^3$ is H, alkyl, aryl, or aralkyl, as described for $R^2$ above; and
$R^4$ is H, alkyl, preferably containing from about 1 to about 20 carbon atoms, such as methyl, ethyl, isopropyl, and hexyl; alkoxy, preferably containing from about 1 to about 20 carbon atoms, such as methoxy and ethoxy; amino; halogen such as chloride and bromide; sulfide; sulfoxide; sulfonate; or heterocyclic, preferably a 5- to 7-membered ring which may be saturated, such a pyrrolidine, morpholine, piperidine, tetrahydrofurane, dioxane, and quinaldine, or unsaturated, such as pyrrole, isoxazole, imidazole, isothiazole, furazan, and pyrazoline.

It is noted that throughout the specification and claims the terms "alkyl", "aryl", and "arylene" include substituted alkyl, aryl, and arylene, such as methoxy ethyl, chlorophenyl, and bromonaphthyl.

Examples of polymers useful for the parent filing x-ray intensifying screen include:
poly[1-naphthyl carbinyl methacrylate-co-S-(1-naphthyl carbinyl)thioacrylate];
poly[1-naphthyl carbinyl methacrylate-co-1-bromo-2-naphthylacrylate];
poly[S-(1-naphthyl carbinyl)thioacrylate-co-benzyl methacrylate];
poly[S-(2-naphthyl carbinyl)thioacrylate-co-benzyl methacrylate]; and
poly[t-butyl methacrylate].

In an especially preferred embodiment, the polymer of the parent filing intensifying screen comprises from 5 to 100 mole percent of a polymerized copolymerizable naphthyl carbinyl methacrylate monomer, and from 0 to 95 mole percent of a polymerized copolymerizable naphthyl carbinyl thioacrylate monomer. In a still further embodiment, the polymer comprises from 5 to 100 mole percent of polymerized 1-naphthyl carbinyl methacrylate and from 0 to 95 mole percent of polymerized S-(1-naphthyl carbinyl)thioacrylate.

The x-ray intensifying screen of the parent filing, comprising a substantially isotropic phosphor, which is excited by x-rays and substantially transparent to light emitted by the phosphor, and a polymeric binder carefully selected so as to match, with 0.02, the index of refraction of the phosphor, is highly transparent. The intensifying screens of the parent filing generally exhibit a mean free path for light scatter greater than one millimeter, preferably greater than 3 millimeters, for phosphor:binder ratios of 2.5 or larger. This highly transparent screen material allows the use of relatively thick screens which absorb more of the incident x-ray beam, and thus results in higher speed. Further, the increased absorption of x-rays decreases quantum mottle and allows improvement in overall image quality. Further still, the polymeric binder protects the fragile phosphors from physical damage.

The support for the x-ray intensifying screen of the parent filing includes any material having an index of refraction equal to that of the phosphor of the parent filing, and having a reflection optical density of at least 1.7 to light emitted by the phosphor. Suitable support materials include polymeric materials such as Lucite ® (poly(methyl)methacrylate); Elbite (tourmaline); Formica ® (poly(urea)formaldehyde resin); polyolefins such as polyethylene and polypropylene; polycarbonates; cellulose acetate; cellulose acetate butyrate; poly(ethylene terephthalate); glass such as Corning Fotoform ® glass having 80 percent of its area covered with holes 0.015 inch deep and 0.005 inch in diameter; and metal such as black anodized aluminum.

The required reflection optical density of 1.7 to light emitted by the phosphor is provided by the use of support materials which are inherently darkly colored, materials which have been dyed or pigmented during manufacture to provide a uniform dark color throughout, or materials which have undergone a surface treatment such as coating with a dye, pigment, or dyed or pigmented material, anodizing in the case of metals, or a combination of the above surface treatments.

The support of the parent filing also has an index of refraction equal to or up to 0.05 units higher than the index of refraction of the phosphor at its wavelength of maximum emission. In one embodiment, a preferred support having both the required optical density and the required index of refraction comprises a conventional support material having a thin polymeric layer on the surface on which the fluorescent composition is to be applied. This thin polymeric layer comprises a polymer having an index of refraction equal to or up to 0.05 units higher than the index of refraction of the phosphor at its wavelength of maximum emission, and a finely divided pigment such as carbon in an amount sufficient to produce an optical density of 1.7 to light emitted by the phosphor.

The x-ray intensifying screen of the parent filing comprising a highly transparent screen material having high speed and a light absorbing support having the required reflection optical density, gives high contrast and resolution. The use of a support which has the same or very slightly higher (up to 0.05 higher) index of refraction as that of the phosphor layer decreases the flare of the image and increases contrast.

In another embodiment of the parent filing, a particularly advantageous fluorescent composition comprises:
(a) from 50 to 90 percent by weight of a substantially isotropic phosphor which is excited by x-rays and substantially transparent to light emitted by said phosphor; and
(b) from 10 to 50 percent by weight of a polymer having an index of refraction within 0.02 of the index of refraction of said phosphor over at least 80 percent of the emission spectrum of said phosphor, said polymer comprising:
(i) from 5 to 99 mole percent of recurring units having the formula:

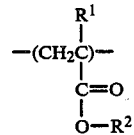

wherein:
$R^1$ and $R^2$ are as described for the polymer of the novel x-ray intensifying screen; and
(ii) from 1 to 95 mole percent of recurring units having the formula:

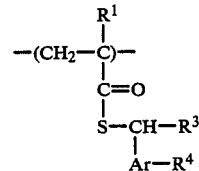

wherein:
Ar, $R^1$, $R^3$, and $R^4$ are as described for the polymer of the parent filing x-ray intensifying screen.

Examples of polymers useful in the parent filing fluorescent composition include:

poly[1-naphthyl carbinyl methacrylate-co-S-(1-naphthyl carbinyl)thioacrylate;
poly[S-(1-naphthyl carbinyl)thioacrylate-co-benzyl methacrylate]; and
poly[S-(2-naphthylcarbinyl)thioacrylate-co-benzyl methacrylate].

Preferred polymers which are useful in the parent filing fluorescent composition include polymers comprising from 5 to 99 mole percent of a polymerized copolymerizable naphthyl carbinyl methacrylate monomer, and from 1 to 95 mole percent of a polymerized copolymerizable naphthyl carbinyl thioacrylate monomer. Especially preferred is a polymer comprising from 5 to 99 mole percent of recurring units having the formula:

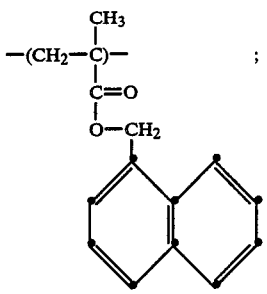

and from 1 to 95 mole percent of recurring units having the formula:

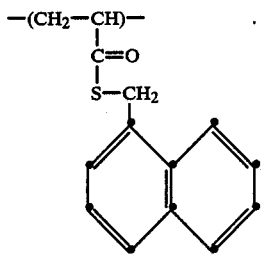

The recurring units for the polymer and their relative proportions are generally selected to achieve the index of refraction previously described.

In a further embodiment of the parent filing, a process for making an intensifying screen comprises the steps of (a) coating a mixture comprising:
  (i) from 50 to 90 percent by weight of a substantially isotropic phosphor which is excited by x-rays and substantially transparent to light emitted by said phosphor; and
  (ii) from 10 to 50 percent by weight of at least one copolymerizable monomer or mixture of monomers, said monomer or mixture of monomers, when polymerized, having an index of refraction within 0.02 of the index of refraction of said phosphor over at least 80 percent of the emission spectrum of said phosphor,
on a support having an index of refraction equal to or up to 0.05 units higher than the index of refraction of said phosphor and having a reflection optical density of at least 1.7 to light emitted by said phosphor; and
(b) polymerizing said mixture coated on said support to produce a polymer comprising recurrent units of said monomer or monomer mixture.

The mixture comprising the fluorescent composition of the parent filing intensifying screen is preferably prepared by combining a substantially isotropic phosphor in the form of a free flowing powder in a polymerizable monomer or mixture of copolymerizable monomers which, when polymerized, exhibit the required index of refraction. The useful phosphor to monomer ratio varies widely, but preferable ranges are from 50:50 to 90:10 by weight, and more preferably in the range from 70:30 to 80:20 by weight. Generally, the phosphor to monomer ratio is maximized, resulting in a honey like, viscous mixture, which is capable of being poured. The resulting mixture is optionally degassed to remove trapped air bubbles.

The mixture optionally further comprises from 0.001 to 1.0 percent by weight, preferably from 0.1 to 0.5 percent by weight of photoinitiator such as 4,4'-bis-chloromethyl benzophenone, benzoin methyl ether, and benzoyl peroxide. It is noted that further additional components are optionally included in the mixtures of the parent filing process. For example, resins, stabilizers, surface active agents and mold release agents serve to improve film formation, coating properties, adhesion of the mixture to the support, separability of the mixture from non-support materials, mechanical strength and chemical resistance.

The mixture of the parent filing process is coated onto the support to a predetermined thickness by techniques well known in the art, such as roll coating, brush coating, solvent coating or x-hopper coating. One method of coating the mixture comprises pouring the mixture onto the desired support, covering it with a cover sheet, such as a glass cover sheet, having appropriate spacers to produce a predetermined coating thickness, and spreading the mixture by applying pressure to the cover sheet to the limit of the spacers.

The optimum coating thickness of the phosphor/monomer mixture depends upon such factors as the use to which the coating will be put, the speed desired, the degree of image quality desired, the phosphor selected, the monomer or monomer mixture employed, the phosphor to monomer ratio, and the nature of other components which may be present in the coating. Useful coating thicknesses for use in preparing x-ray intensifying screens are from 25 to 2500 microns, with coating thicknesses of from 400 to 1200 microns being preferred. The preferred coating coverage likewise varies widely between about 10 g and about 500 g/ft$^2$, with the range from 50 to 200 g/ft$^2$ being preferred.

The coating, comprising a monomer or mixture of monomers and a phosphor, is preferably polymerized at a temperature of 20°-30° C. by irradiation with a near-ultraviolet lamp. Other methods of polymerization are similarly used. Such methods include thermal polymerization, polymerization by electron beam radiation, and polymerization by high energy gamma irradiation.

After polymerization, the polymerized mixture is preferably cooled to room temperature or below, and any cover sheet used to spread the coated mixture and establish coating thickness is removed. In some cases, release is gently initiated, by inserting a blade between the support and the cover sheet to separate the support from the coated polymerized mixture, until Newton's rings are observed at the initiation site. The cover sheet is then lifted away, optionally further cooling the cover sheet briefly, for example, with powdered dry ice. Further cooling should be carefully undertaken, however, as overcooling the cover sheet is likely to shatter the polymerized, coating screen mixture.

The resulting polymer has an index of refraction within 0.02 of the index of refraction of the phosphor over 80 percent of its emission spectrum, thus maintaining a high degree of transparency to the light emitted by the excited phosphor. The polymer protects the phosphor from mechanical damage, and, if hydrophobic, from damage caused by moisture.

The process of the parent filing thus provides a highly transparent x-ray intensifying screen having satisfactory speed, high contrast, and high resolution; Further, the process as described provides a relatively inexpensive and straightforward method of manufacturing high speed, high resolution x-ray intensifying screens without the addition of reflecting pigments.

EXAMPLES

The following preparations and examples are included for a further understanding of the invention.

PREPARATION 1

The phosphor RbI:Tl (0.0004) was prepared by adding a solution of 0.33 g of thallous acetate in 500 ml of isopropanol at a rate of 36 ml/min to a vigorously stirred solution of 636 g rubidium iodide in 460 g of water. The temperature of the isopropanol solution was maintained at $-29°$ C., and the temperature of the aqueous solution was maintained at about 15° C. 200 g of the precipitated rubidium iodide phosphor was collected, carefully removing all of the supernatant isopropanol water mixture, which was reserved for recovery of unprecipitated rubidium iodide to be used in subsequent preparations. (Any supernatant isopropanol/water mixture remaining with the precipitated phosphor can contaminate the precipitated phosphor with further precipitation of a phosphor differing in composition, and cause unwanted scattering of light in the resulting fluorescent composition.) The precipitated thallium-activated RbI phosphor, being free of supernatant isopropanol/water mixture, was then washed twice with isopropanol in a high speed, food processing blender, and the precipitate collected on glass filter paper after each washing. The phosphor was vacuum dried and bottled. The speed of the RbI:Tl (0.0004) thus prepared was about equal to that of KI:Tl, and speeds between 6 and 7 times greater than that of DuPont No. 501 commercial CaWO$_4$ phosphor were obtained in the x-ray powder test described in U.S. Pat. No. 3,668,142, previously referred to herein.

PREPARATION 2

The phosphor KI:Tl (0.0003) was prepared by adding a solution of 0.4 g thallous acetate in 1.6 liters of isopropanol at $-29°$ C. to a solution of 800 g potassium iodide in 600 g distilled water at 15° C. with vigorous stirring. The temperature of the supernatant solution was maintained at about 14° C. The rate of addition was 35 ml/min. The crystals of the precipitated phosphor were free from defects and had cubic morphology with crystal sizes in the range from about 10 to 20 microns. The speed of the phosphor, measured after precipitation, washing, and drying by the method used in U.S. Pat. No. 3,668,142 was about seven times that of commercial calcium tungstate.

PREPARATION 3

A mixture of 66 g of cyclopentadiene and 500 ml of methylene chloride was stirred with 90 g of acryloyl chloride at dry ice temperature ($-78.5°$ C.) and allowed to warm slowly to room temperature over 24 hours. The reaction product was then distilled. The resulting bicycloheptenecarbonyl chloride was allowed to react with 1-(naphthylcarbinyl)mercaptan and refluxed in methylene chloride (b.p. 40°–41° C.) while one equivalent of di-isopropylethylamine was slowly added to the mixture. The product was vacuum distilled, using a 250° C. oil bath, under which conditions the cyclopentadiene split off, giving S-(1-naphthylcarbinyl)thioacrylate in good yield. A thin layer chromograph (50:50 hexane/ether, silica gel) of the resulting product indicated an R$_f$ value of 0.69 to 0.72.

PREPARATION 4

1-Naphthyl carbinyl methacrylate was prepared by catalytic transesterification of an excess quantity of methyl methacrylate with the alcohol 1-naphthyl carbinol. The by-product, methanol, was continuously removed by azeotropic distillation and/or use of molecular sieves, thus pulling the reversible reaction towards completion. When the reaction was essentially complete, the excess methyl methacrylate was removed by distillation at atmospheric pressure. A small amount (from 5 to 25%) of the unreacted higher alcohol 1-naphthyl carbinol remained in the resulting 1-naphthyl carbinyl methacrylate.

PREPARATION 5

In an alternative synthesis of 1-naphthyl carbinyl methacrylate, 1-(chloromethyl)naphthalene is treated with one equivalent of potassium methacrylate in dimethyl sulfoxide. The potassium methacrylate employed is either previously isolated or formed in situ from potassium hydroxide and methacrylic acid. The reaction is continued at 70° C. for 30 minutes. The resulting 1-naphthylcarbinyl methacrylate is isolated in 93–98% yield, virtually free from contaminants.

PREPARATION 6

Aluminum plates were anodized in 12–15 percent H$_2$SO$_4$ at 70° C. and 12–14 amperes/ft$^2$. The porous deposit was treated with aluminum Black BK ® dye (a registered trademark of Sandoz Colors and Chemicals) and then sealed with hot water or nickel acetate solution. The resulting support exhibited an optical density of 2.34 when overcoated with a mixture of rubidium iodide and polymer having matched indexes of refraction. Although the index of refraction of anodized aluminum is not precisely known, it is thought to be about 1.76, which is less than 0.05 units higher than that of rubidium iodide at 425 nm, the region of maximum emission.

EXAMPLE 1

A mixture of 100 g of thallium-activated potassium iodide phosphor (0.0003), as prepared in Preparation 2, and 40 g of a 4:1 mixture of S-(1-naphthyl carbinyl)thioacrylate, as prepared in Preparation 3, and 1-naphthyl carbinyl methacrylate, as prepared in Preparation 4, containing 0.3 percent by weight of 4,4'-bis-chloromethyl benzoquinone was degassed under vacuum. A portion of the mixture was photopolymerized between two glass sheets to form an unsupported screen, and released. The unsupported screen was placed in a Cary ® 17 spectrophotometer and its optical density was measured using an unsupported screen containing only photopolymerized polymer (lacking the phosphor) as a reference. The optical density of the unsupported screen was used to calculate the mean free path of light through the screen. The mean free path was calculated to be at least 2.3 mm.

Another portion of the mixture was coated at different thicknesses on a black anodized aluminum support as prepared in Preparation 6, and photopolymerized under glass cover sheets. Radiographs were made by exposing Lo-Dose ® film in contact with these experimental supported screens as back screens with 70 kVp x-rays. A control radiograph was made by likewise exposing Lo-Dose ® film in contact with a DuPont Par Speed ® Intensifying screen in order to obtain the relative speeds of the experimental screens. The difference in speed was calculated through the known density vs. log exposure curve for Lo-Dose ® film from the densities which resulted on the exposed and developed films. The following results were obtained.

| Screen Thickness (microns) | Screen Coverage g/ft2 | Relative Speed PAR = 100* | 10 micron lead bar test object Resolution |
| --- | --- | --- | --- |
| 405 | 61 | 175 | 3.15 lp/mm |
| 750 | 113 | 265 | 2.24–2.5 |
| 1115 | 168 | 325 | 2.0 |

*DuPont Par Speed ® Intensifying Screen

EXAMPLE 2

A mixture of 35.5 g of the thallium-activated rubidium iodide phosphor (0.0004) as prepared in Preparation 1 and 10 g of a 60:40 mixture of 1-naphthyl carbinyl methacrylate an 1-bromo-2-naphthylacrylate containing 0.3 percent 4,4'-bis-chloromethyl benzophenone was spread on black anodized aluminum support and covered with a glass sheet while being photopolymerized. When polymerization was complete, the glass sheet was released. The resulting transparent screen was 500 microns thick and a coverage of 89 g of phosphor per square foot. Radiographs made with this screen as a back screen with Lo-Dose ® Film at 70 kVp gave a relative radiographic speed (calculated as in Example 1) of 255 compared to 285 for a DuPont Hi-Plus ® Screen with Lo-Dose ® Film. When a bone and bead test object was employed in the same comparison, better image quality was obtained with the transparent screen.

EXAMPLE 3

A mixture of 250 g of the thallium-activated rubidium iodide and 65 g of a 3:1 mixture of 1-naphthyl carbinyl methacrylate and S-(1-naphthyl carbinyl)thioacrylate which also contained 0.3 percent by weight of 4,4'-bis-chloromethyl benzophenone was degassed under vacuum and then coated three ways: (1) on black anodized aluminum support, (2) on reflective aluminum support on an optically flat surface, and (3) on no support (self supporting film).

All three coatings were of equal thickness and were photopolymerized. Radiographs were made with these three screens, along with the DuPont Hi-Plus ® screen, using Lo-Dose ® Film, 70 kVp x-ray and a 20μ lead bar test object. The resolution of the radiographs was as follows:

| | |
| --- | --- |
| Hi-Plus ® Screen | 4.0 lp/mm |
| Black Aluminum Support | 4.0 lp/mm |
| Reflective Aluminum Support | 1.8 lp/mm |
| Unsupported | 1.8 lp/mm |

The resolution of the screen having a black support showed a dramatic increase both over the resolution of the screen having a reflective support and over that of the unsupported screen.

EXAMPLE 4

A mixture of 136.8 g of thallium-activated rubidium iodide (0.0004), 40.0 g of a 3:1 mixture of 1-naphthyl carbinyl methacrylate containing up to 25 percent 1-naphthyl carbinol and S-(1-naphthyl carbinyl)thioacrylate, and 0.3 percent by weight of 4,4'-bis-chloromethyl benzophenone was degassed under vacuum. The mixture was then coated on a support consisting of inlaid strips of black polished Formica ®, black anodized aluminum, black Corning Fotoform ® glass having 80 percent of its area covered with holes, 0.005 inch in diameter and 0.015 inch deep, and dark blue tourmaline in a matrix of black Lucite ® plastic. The mixture was spread evenly across the support so that the different types of support were coated with an equal thickness of the mixture. A glass cover sheet was placed on the mixture, and the mixture was photopolymerized. The cover sheet was removed, and the reflection optical densities of the different areas were measured. A 70 kVp radiograph of a 10 micron lead bar resolution test object was made using the screen as a back screen with DuPont Lo-Dose ® film. The radiograph made using this transparent screen was compared with a control radiograph made with Lo-Dose ® film and using an opaque Hi-Plus ® screen. Radiographic speed was determined as in Example 1. The results obtained were as follows:

| Support | Refractive Index $n_d$ | Reflection Optical Density | Radiographic Speed | Resolution (lp/mn) |
| --- | --- | --- | --- | --- |
| Lucite ® | 1.49 | 2.25 | 315 | 2.5–2.8 |
| Fotoform ® Glass | — | 1.87 | 250 | 3.15 |
| tourmaline | 1.64 | 2.57 | 250 | 3.15 |
| Formica ® | 1.65 | 2.17 | 245 | 3.15–3.55 |
| Black anodized Aluminum | 1.76 | 2.34 | 245 | 3.55 |
| Hi-Plus ® Screen Control (opaque) | — | — | 285 | 3.55 |

The results indicated that the optimum combination of speed and resolution were obtained when the fluorescent composition mixture was coated on a black anodized aluminum surface for the particular transparent phosphor-polymer combination selected. Further, the results showed that the transparent screen having a black anodized aluminum support exhibited resolution equal to and radiographic speed nearly equal to the conventional opaque control screen; however, the transparent screen of the invention displayed less quantum mottle than the conventional opaque screen.

EXAMPLE 5

A mixture of 180 g of finely powdered $Ba_{0.94}Sr_{0.06}FCl:Eu$ (0.0006) phosphor and 51 g of a blend of benzyl methacrylate and 1-naphthylcarbinyl methacrylate (approximately 50:50 by weight) was degassed under vacuum and spread on a black anodized aluminum support. A glass cover sheet was placed on top of the layer and the mixture was polymerized by irradiation with an ultraviolet lamp with substantial emission at 365 nm through the glass. After the glass was removed, the area of the layer and the weight were recorded. Coverage of the screen was calculated at 85 g/ft² of phosphor. The mean free path for 380 nm radiation was measured spectrophotometrically as 304 microns.

The screen was used as a back screen with a 58 g/ft² Gd$_2$O$_2$S:Tb (on a highly reflecting support) front screen to make 70 kVp radiographs of a standard "bone and bead" test object with KODAK X-OMAT R ® x-ray film. The control for the image quality evaluations was made with both front and back Gd$_2$O$_2$S:Tb screens. The speed of the control was 400 and the resolution was 2.24 lp/mm. The transparent back screen gave a speed of 350 and a resolution of 2.24 lp/mm. The mottle of both radiographs was judged about equal, but the sharpness and bead visibility were superior in the transparent screen radiograph.

The invention has been described in detail with particular reference to preferred embodiments thereof, but it will be understood that variations and modifications can be effected within the spirit and scope of the invention.

What is claimed is:

1. A method of storing an image produced by x-ray exposure and releasing the stored image comprising:
   exposing an x-ray storage screen, comprised of an isotropic storage phosphor and a polymer coated on a support, to x-radiation of a first wavelength in an imagewise manner to store an image pattern in the storage screen,
   retrieving the image pattern from the storage screen by exposing the storage screen to radiation of a second wavelength, thereby stimulating radiation of a third wavelength,
   the polymer having an index of refraction which matches that of the phosphor at the second wavelength, and
   the support being non-reflective to radiation of the second wavelength.

2. A method of storing an image according to claim 1 wherein the index of refraction of the polymer does not match the index of refraction of the phosphor for radiation of the third wavelength.

3. A method of storing an image according to claim 1 wherein the index of refraction of the polymer differs by more than 0.02 from the index of refraction of the phosphor for radiation of the third wavelength.

4. A method of storing an image according to claim 1 wherein the support is reflective to radiation of the third wavelength.

5. A method of storing an image according to claim 1 wherein the support exhibits minimum reflectance to radiation of the second wavelength.

6. A method according to claim 1 wherein the phosphor and the polymer form a fluorescent composition comprising
   (a) from 50 to 90 percent by weight of the phosphor and
   (b) from 10 to 50 percent of the polymer.

7. A method according to claim 6 wherein the polymer comprises:
   (i) from 5 to 100 mole percent of a copolymerizable ethylenically unsaturated monomer; and
   (ii) from 0 to 95 mole percent of recurring units having the formula

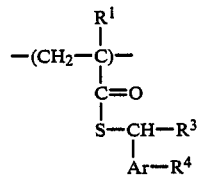

wherein:
Ar is arylene;
R$^1$ is H or alkyl;
R$^2$ is H, alkyl, aryl, or aralkyl; and
R$^4$ is H, alkyl, alkoxy, amino, halogen, sulfide, sulfoxide, sulfonate or heterocyclic.

8. A method according to claim 6 wherein the polymer comprises:
   (i) from 5 to 100 mole percent of recurring units having the formula:

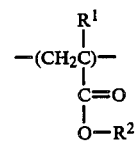

wherein:
R$^1$ is H or alkyl; and
R$^2$ is alkyl, cycloalkyl, aryl, aralkyl or aryl substituted with alkyl, alkoxy or heterocyclic; and
   (ii) from 0 to 95 mole percent of recurring units having the formula:

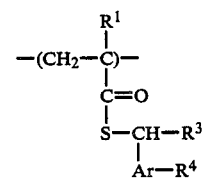

wherein:
Ar is arylene;
R$^3$ is H, alkyl, aryl, or aralkyl; and
R$^4$ is H, alkyl, alkoxy, amino, halogen, sulfide, sulfoxide, sulfonate or heterocyclic.

9. A method according to claim 6 wherein the polymer comprises:
   (i) from 5 to 99 mole percent of recurring units having the formula:

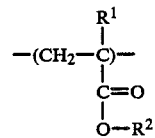

wherein:
R$^1$ is H or alkyl; and
R$^2$ is alkyl, cycloalkyl, aryl, aralkyl or aryl substituted with alkyl, alkoxy, or heterocyclic; and
   (ii) from 1 to 95 mole percent of recurring units having the formula:

$$-(CH_2-C)- \\ \quad | \\ \quad R^1 \\ \quad | \\ \quad C=O \\ \quad | \\ \quad S-CH-R^3 \\ \qquad | \\ \qquad Ar-R^4$$

wherein
Ar is arylene;
$R^1$ is H or alkyl;
$R^3$ is H, alkyl, aryl, or aralkyl and
$R^4$ is H, alkyl, alkoxy, amino, halogen, sulfide, sulfoxide, sulfonate or heterocyclic.

10. An x-ray storage screen comprising:
(a) a substantially isotropic storage phosphor, said phosphor being excitable by radiation of a first wavelength and, when thereafter said screen is exposed to radiation of a second wavelength, said phosphor emits radiation of a third wavelength; and
(b) a polymer having an index of refraction which matches that of said phosphor at the second wavelength; and
(c) said support being non-reflective to radiation of the second wavelength,
said phosphor and said polymer forming a fluorescent composition comprising
(a) from 50 to 90 percent by weight of said phosphor and
(b) from 10 to 50 percent by weight of said polymer, and
said polymer comprising:
(i) from 5 to 99 mole percent of recurring units having the formula:

$$-(CH_2-C)- \\ \quad | \\ \quad CH_3 \\ \quad | \\ \quad C=O \\ \quad | \\ \quad O-CH_2-\text{(naphthyl)}$$ ;

(ii) from 1 to 95 mole percent of recurring units having the formula:

$$-(CH_2-CH)- \\ \qquad | \\ \qquad C=O \\ \qquad | \\ \qquad S-CH_2-\text{(naphthyl)}$$

11. An x-ray storage screen comprising:
(a) a substantially isotropic storage phosphor, said phoshor being excitable by radiation of a first wavelength and, when thereafter said screen is exposed to radiation of a second wavelength, said phosphor emits radiation of a third wavelength; and
(b) a polymer having an index of refraction which matches that of said phosphor at the second wavelength; and
(c) said support being non-reflective to radiation of the second wavelength,
said phosphor and said polymer forming a fluorescent composition comprising
(a) from 50 to 90 percent by weight of said phosphor and
(b) from 10 to 50 percent by weight of said polymer, and
said polymer comprising:
(i) from 5 to 100 mole percent of a copolymerizable naphthyl carbinyl methacrylate monomer; and
(ii) from 0 to 95 mole percent of a copolymerizable naphthyl carbinyl thioacrylate monomer.

12. An x-ray storage screen comprising:
(a) a substantially isotropic storage phosphor, said phosphor being excitable by radiation of a first wavelength and, when thereafter said screen is exposed to radiation of a second wavelength, said phosphor emits radiation of a third wavelength; and
(b) a polymer having an index of refraction which matches that of said phosphor at the second wavelength; and
(c) said support being non-reflective to radiation of the second wavelength,
said phosphor and said polymer forming a fluorescent composition comprising
(a) from 50 to 90 percent by weight of said phosphor and
(b) from 10 to 50 percent by weight of said polymer, and
said polymer comprising
(i) from 5 to 99 mole percent of a copolymerizable naphthyl carbinyl methacrylate monomer; and
(ii) from 1 to 95 mole percent of a copolymerizable naphthyl carbinyl thioacrylate monomer.

13. An x-ray storage screen comprising:
(a) a substantially isotropic storage phosphor, said phosphor being excitable by radiation of a first wavelength and, when thereafter said screen is exposed to radiation of a second wavelength, said phosphor emits radiation of a third wavelength; and
(b) a polymer having an index of refraction which matches that of said phosphor at the second wavelength; and
(c) said support being non-reflective to radiation of the second wavelength,
said phosphor and said polymer forming a fluorescent composition comprising
(a) from 50 to 90 percent by weight of said phosphor and
(b) from 10 to 50 percent by weight of said polymer, and
said polymer comprising:
(i) from 5 to 100 mole percent of polymerized 1-naphthyl carbinyl methacrylate monomer; and
(ii) from 0 to 95 mole percent of polymerized S-(1-naphthyl carbinyl)thioacrylate monomer.

14. An x-ray storage screen according to claim 16 wherein said fluorescent composition is coated on a black anodized aluminum surface of said support.

* * * * *